(12) United States Patent
Weiss et al.

(10) Patent No.: US 8,170,672 B2
(45) Date of Patent: May 1, 2012

(54) ELONGATED IMPLANT HAVING AN EXTERNAL ENERGY COUPLING

(75) Inventors: Ingo Weiss, Berlin (DE); Thomas Doerr, Berlin (DE); Andreas Neumann, Berlin (DE); Erhard Flach, Berlin (DE); André Burch, Bachenbuelach (CH)

(73) Assignee: Biotronik CRM Patent AG, Baar (CH)

( * ) Notice: Subject to any disclaimer, the term of this patent is extended or adjusted under 35 U.S.C. 154(b) by 253 days.

(21) Appl. No.: 12/467,988

(22) Filed: May 18, 2009

(65) Prior Publication Data
US 2009/0306738 A1    Dec. 10, 2009

(30) Foreign Application Priority Data

Jun. 5, 2008    (DE) .................... 10 2008 002 228

(51) Int. Cl.
*A61N 1/378*    (2006.01)
(52) U.S. Cl. ................. 607/33; 607/9; 607/61; 607/119
(58) Field of Classification Search .......... 607/2, 9, 607/31, 33, 36, 37, 45, 61, 116, 117, 119
See application file for complete search history.

(56) References Cited

U.S. PATENT DOCUMENTS

| | | | |
|---|---|---|---|
| 5,193,540 A | | 3/1993 | Schulman et al. |
| 5,991,664 A | * | 11/1999 | Seligman ..................... 607/60 |
| 6,141,588 A | * | 10/2000 | Cox et al. ..................... 607/9 |
| 2002/0095191 A1 | | 7/2002 | Bulkes et al. |
| 2004/0088024 A1 | | 5/2004 | Firlik et al. |
| 2006/0058588 A1 | * | 3/2006 | Zdeblick ..................... 600/300 |
| 2006/0085041 A1 | | 4/2006 | Hastings et al. |
| 2006/0085042 A1 | * | 4/2006 | Hastings et al. ............. 607/33 |
| 2006/0136004 A1 | * | 6/2006 | Cowan et al. ................ 607/33 |
| 2008/0021505 A1 | | 1/2008 | Hastings et al. |
| 2008/0077184 A1 | | 3/2008 | Denker et al. |
| 2008/0109054 A1 | | 5/2008 | Hastings et al. |

FOREIGN PATENT DOCUMENTS

| | | |
|---|---|---|
| WO | WO 2007/149462 | 12/2007 |
| WO | WO 2008/034005 | 3/2008 |

OTHER PUBLICATIONS

German Search Report, dated Mar. 20, 2009.
European Search Report, dated Jul. 29, 2009.

* cited by examiner

*Primary Examiner* — Carl H Layno
*Assistant Examiner* — Eugene Wu
(74) *Attorney, Agent, or Firm* — ARC IP Law, PC; Joseph J. Mayo

(57) ABSTRACT

Electrotherapeutic implant for stimulation of body tissue, comprising at least two electrode poles (14) which are connected to electric feeder lines, a demodulation unit (22), at least one electric feeder line (20), which is designed as an antenna and contacts the demodulation unit (22), wherein the implant (10) is fabricated from one piece, can be affixed (16) at the treatment site and is equipped with a biocompatible insulation, whereby the components of the implant (10) are designed so that a therapeutic energy which can be injected from the outside over the antenna (20) during the treatment is delivered to the therapeutic target region without intermediate storage.

14 Claims, 8 Drawing Sheets

ELONGATED IMPLANT HAVING AN EXTERNAL ENERGY COUPLING

This application takes priority from German Patent Application DE 10 2008 002 228.4, filed 5 Jun. 2008, the specification of which is hereby incorporated herein by reference.

BACKGROUND OF THE INVENTION

1. Field of the Invention

The invention relates to an electrotherapeutic implant for stimulation of body tissue. Fields of use for such instruments include in particular spinal cord stimulation. Subcutaneous stimulation (electroacupuncture), muscle stimulation, heart stimulation and brain stimulation. Preferred fields of use of the inventive implant for cardiac applications include in particular right-ventricular applications in the ventricles and left-ventricular application in the vessels but also epicardial applications. The present invention relates in particular to an electrotherapeutic implant that can receive the therapeutic energy required for electrotherapeutic treatment of body tissue from outside of the body.

2. Description of the Related Art

Such implants are known in principle, but they have a number of disadvantages. The size and shape (length-width-height relationship) of electrotherapeutic implants according to the state of the art are determined essentially by the size and shape of the battery.

However, batteries often cannot be accommodated directly at the treatment site because of their size and shape.

For this reason, electrotherapeutic implants according to the state of the art are often designed in two parts and also include, in addition to a housing which accommodates the battery and other electronic components, separate electrodes which are connected to the electronic components inside the housing by electric feeder lines.

The housing for such implants is normally positioned at a site remote from the treatment, e.g., beneath the pectoral muscles. The desired stimulation is achieved via electrodes placed at the treatment site and connected to the electronic components of the housing. The housing sends the required therapeutic energy over the electric feeder lines during the stimulation.

An implantable device according to the state of the art appears bulky because of its size and shape, in particular because of the size and shape of the battery, and is especially problematical in many areas of the body (e.g., when the patient is lying on it).

BRIEF SUMMARY OF THE INVENTION

The object of the present invention is thus to eliminate the disadvantages arising from the state of the art, in particular those based on the comfort of the patient with the implant.

According to the invention, this object is achieved by an electrotherapeutic implant, comprising:
  at least two electrode poles connected to electric feeder lines,
  a demodulation unit and
  at least one electric feeder line, which is designed as an antenna and contacts the demodulation unit,
wherein the implant is characterized in that
  it is manufactured from one piece having a compact closed outer shape,
  has means for securing it at the treatment site and
  is provided with a biocompatible insulation (e.g., polymer silicone, polyurethane, polyimides, parylene or the like), whereby
  the components of the implant are designed to deliver a therapeutic energy, which can be injected from the outside over the antenna during the treatment without temporary storage via the electrode poles, to the therapeutic target region.

According to another inventive idea, the inventive implant is part of a system that has an external pulse generator, which is itself also another inventive idea for providing the therapeutic energy to be injected.

This external pulse generator is designed to inject a therapeutic energy into the implant by means of contactless energy transfer in the event of treatment. For this reason, the external pulse generator has at least one antenna for electromagnetic transmission of a high-frequency alternating voltage.

Since the therapeutic energy is preferably injected into the implant as a high-frequency alternating voltage, the implant has a demodulation unit to allow delivery of a demodulated pulse via the electrode poles.

According to an especially simple embodiment, the demodulation unit is a diode which is connected to the feeder line for the first electrode on one side and to the feeder line for the second electrode on the other side.

The electrodes of the implant are preferably coated with an electrochemically active coating of iridium, iridium oxide, carbon or titanium nitride.

The feeder lines to the electrodes function as antennas. In the event of treatment, a high-frequency alternating voltage injected over the antenna is rectified through the diode, demodulated and delivered over the two electrode poles.

Especially preferably at least the feeder line of the implant which is designed as an antenna is a coil or a cable of stainless steel, MP35N, DFT wire, conductive plastic, carbon fibers, conductive fluids or conductive gels.

The inventive implant preferably has a shape, such that it is adapted to the anatomical details of the target region.

The inventive implant especially preferably has an elongated shape, such that the ratio of its length dimensions to transverse dimensions is especially preferably >10. The implant is especially preferably essentially cylindrical and is designed with a circular cross section.

According to an especially preferred embodiment, the implant has a diameter of less than 3.3 mm.

To ensure the most pleasant possible comfort of the patient wearing the implant, it is preferably designed to be mechanically flexible and it may also adapt to the body during movement.

To be protected from dysfunctions even after the implant has been in a patient's body for a long time, all the connections of the implant are preferably designed to be fatigue-proof.

According to a preferred embodiment variant, the implant has means for affixing it at the treatment site so as to nevertheless be affixable at the desired treatment site. The implant especially preferably has at least one loop or eye in a proximal area of the implant by means of which it can be sutured on the body tissue as well as via a distally arranged anchoring element, e.g., tines, a fixation screw, a helix, a balloon, a stent-like device or a preform in a distal region of the implant, which can produce a form-fitting closure together with the vascular branching.

In addition to its elongated shape, which is especially preferably cylindrical, with an especially preferably isodiametric cross-sectional course over the entire length, the implant according to another embodiment variant has a section with an enlarged diameter in which larger individual electronic components are accommodated.

The section of the enlarged outside diameter is of dimensions such that the elongated implant can nevertheless be inserted into blood vessels.

According to another embodiment variant, the implant is not designed isodiametrically over the entire course but instead tapers in cross section to a distal end, which can be inserted especially easily into a blood vessel because of its tapering cross section and can be advanced to especially far into blood vessels, which become thinner toward the periphery.

To further facilitate placement of the implant at the treatment site, according to another embodiment, means are proposed for controlling the implant inside the body or body cavities. According to an embodiment variant, a lumen that is continuous in the longitudinal direction is provided to receive a guide wire for this purpose. To bring the implant to the treatment site, in such a case a guide wire is first inserted into a blood vessel and then the inventive implant is advanced over the guide wire until it has reached its desired position.

According to an especially preferred embodiment variant, the implant has an enable device which allows the therapeutic energy received over the antenna to be delivered only on receiving a suitable enable code.

A check of the admissibility of an enable action serves to allow exclusively a therapeutic energy which is provided for treatment purposes and has been injected via the antenna of the implant to be delivered via the electrode poles.

If a therapeutic energy is inadvertently injected into the implant, the electrode poles are not enabled because the required enable code is not available.

According to one embodiment variant, the code required for enabling the electrode poles can be received over the antenna for coupling of the therapeutic energy. According to an alternative preferred embodiment, a second antenna is provided, which is designed to receive control signals and/or enable codes.

According to an especially simple embodiment variant, the enable device is formed by a field effect transistor, which first blocks the delivery of therapeutic energy via the electrode poles. With the field effect transistor, the second antenna in this embodiment is connected to the field effect transistor in such a way that the control signals and/or enable codes received over the antenna control the enabling of the electrode poles with the help of the barrier layer of the field effect transistor.

If sufficient power is injected over the antenna for reception of control signals and/or enable codes, the field effect transistor enables the electrode poles and the therapeutic energy is delivered to the body tissue that is to be stimulated in the event of treatment.

According to a preferred embodiment variant, the field effect transistor is a JFET transistor.

A separate embodiment of an antenna for receiving control signals and/or enable codes is advantageous because it is possible in this way to design this antenna for a different resonant frequency than the antenna for coupling of the therapeutic energy. In this way, it is possible to eliminate subsequent filtering of control signals and/or enable codes out of a signal containing the therapeutic energy. According to an alternative embodiment variant, however, the implant may also be designed for filtering out control signals and/or enable codes from a signal containing the therapeutic energy.

Instead of a second antenna, the implant may also have means for receiving control signals, which are sent in the form of a modulated magnetic field or by ultrasound from the outside.

To prevent a control signal and/or an enable code intended for another patient from being erroneously injected into the implant and erroneously causing a therapeutic energy that has been injected into the implant to be delivered via the electrode poles, according to a preferred embodiment variant the inventive implant is designed to enable the electrode poles only on receiving an enable code, which contains an implant-specific individual identifier.

To this end, such an embodiment variant has a control unit which checks the implant-specific individual identifier of a received enable code and allows the electrode poles to be enabled only on receiving correct identifiers.

According to another embodiment variant, the control unit, preferably also including the functions of the demodulation unit and the enable device, is designed to regulate a treatment sequence (triggering the electrode poles, sequence, polarity, pulse parameters, pulse amplitude, etc.) and the duration of treatment on receiving a corresponding control signal.

If the implant has a plurality of electrodes, the control unit is preferably also designed to enable only a certain subgroup of electrode poles for delivering a certain pulse.

For receiving corresponding control signals, the control unit is preferably in turn connected to the antenna for receiving control signals and/or enable codes.

For the power supply, the control unit is preferably connected to the antenna for coupling of the therapeutic energy and utilizes a part of the injected therapeutic energy for its power supply.

According to another embodiment variant, the control unit is designed so that the energy required for supplying power to the control unit is injected over the antenna for transmission of the control signals and/or enable codes.

According to another embodiment variant, the control unit has a temporary energy storage mechanism capable of storing energy injected from the outside for supplying power to the control unit and supplying it continuously to the control unit.

The temporary energy storage mechanism for supplying power to the control unit is connected to the antenna for coupling of control signals and/or enable codes according to an embodiment variant with the antenna for coupling of the therapeutic energy, or according to another embodiment variant, it is connected to the antenna for coupling of control signals and/or enable codes.

According to another embodiment variant, the implant also has a terminal for connection of a traditional heart pacemaker.

In conjunction with a heart pacemaker, the electrode poles of the implant are used as electrode poles to be connected to a traditional heart pacemaker. According to a corresponding embodiment variant, the implant is designed to relay pulses generated by the heart pacemaker to the electrode poles. This embodiment has the advantage that in addition to the signals relayed by the heart pacemaker for certain treatment methods, energy and control signals delivered autarchically to the heart pacemaker can be injected directly into the inventive implant without burdening the energy storage mechanism of the connected heart pacemaker.

According to another embodiment variant, the control unit of the inventive implant also has a measurement device which is designed to transmit patient-specific measured data or instrument-specific measured data determined by sensors to the outside via an antenna.

The measurement device is preferably connected to the antenna for transmission of the control signals and/or enable codes and sends the patient-specific and/or instrument-specific measured data externally via the antenna.

The external pulse generator is equipped with a high-frequency generator and at least one antenna for an external supply of therapeutic energy to the implant, so that therapeutic energy is sent to the implant via the antenna in the use situation.

The pulse generator preferably also has a control unit, with which control signals are generated and can be transmitted to the implant over the antenna for transmission of the therapeutic energy or transmitted via a second antenna of the pulse generator according to a second embodiment variant.

Instead of a second antenna, the pulse generator according to another embodiment is designed to transmit the control signals in the event of treatment to the implant by means of a magnetic field modulated by the control unit of the pulse generator or by ultrasound.

The control signals transmitted to the implant in the event of treatment are preferably enable codes which, as explained above, lead to enabling of the implant in the event of treatment. These enable codes preferably contain implant-specific individual identifiers, so that only an implant that accepts the implant-specific individual identifier transmitted can be enabled with the external pulse generator.

According to another embodiment, the control unit of the pulse generator is designed to generate control signals which contain information about a desired treatment sequence (triggering of electrodes, polarity, pulse parameters, pulse amplitude).

According to another embodiment variant, the pulse generator is designed to receive patient-specific measured data sent by the implant and/or instrument-specific measured data and to analyze and/or store the data, preferably with the help of the control unit of the pulse generator.

For coupling of patient-specific parameters which are needed for generating the enable code or for generating a control signal for controlling the treatment sequence, for example, the inventive pulse generator preferably also has a data input interface.

BRIEF DESCRIPTION OF THE DRAWINGS

Additional aspects of the inventive implant and various embodiment variants are explained on the basis of the drawings, in which.

DETAILED DESCRIPTION OF THE INVENTION

Figure 1:
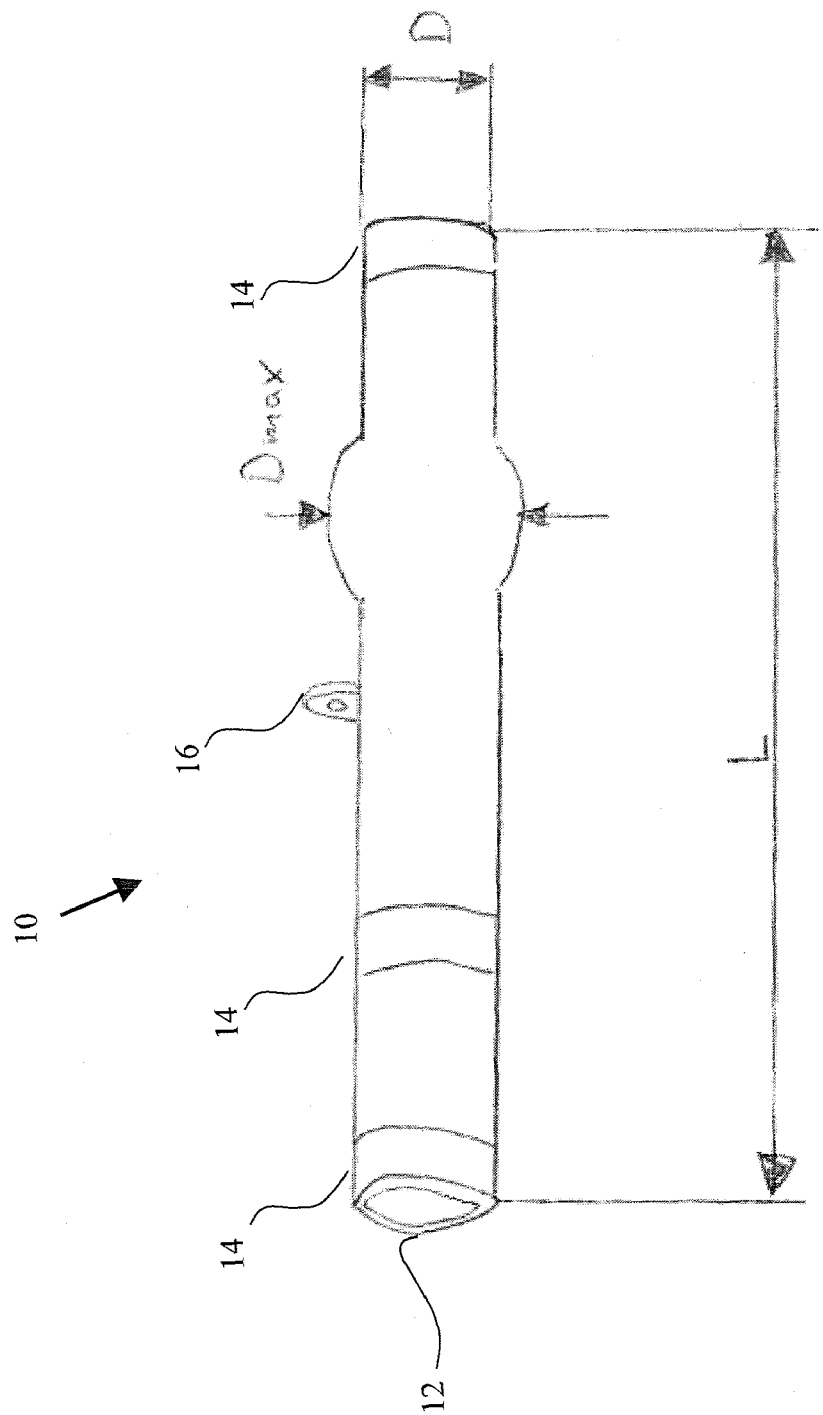
FIG. 1 shows a perspective external view of the inventive implant.

FIG. 1 shows a perspective external view of the inventive implant 10 with the length L and the diameter D according to an especially preferred embodiment variant, in which the implant is embodied as an elongated hollow cylinder having a lumen that is continuous in the longitudinal direction and having a dimension ratio L/D>10.

The embodiment variant of the implant 10 shown in FIG. 1 has a tubular insulator 12 on which are placed a total of three ring-shaped electrodes 14. The electronic components of the implant which are not shown in this figure are embedded in the sheathing of the tubular insulator 12. According to the embodiment variant shown here, the outside diameter of the tubular insulator 12 widens outward in a certain section, which fulfills the purpose that larger electronic components, which could not otherwise be accommodated in the jacket of the tubular insulator 12, find space in this area. However, the diameter $D_{max}$ in this area is smaller than one and one-half times the diameter D of the insulator 12.

To affix the implant 10 at the treatment site, it has a loop 16 by means of which it can be sutured in the body tissue of a patient.

The implant 10 shown with a continuous lumen in FIG. 1 has the advantage that it can easily be advanced to the desired treatment site over a guide wire in a risk-minimizing manner.

Figure 2:
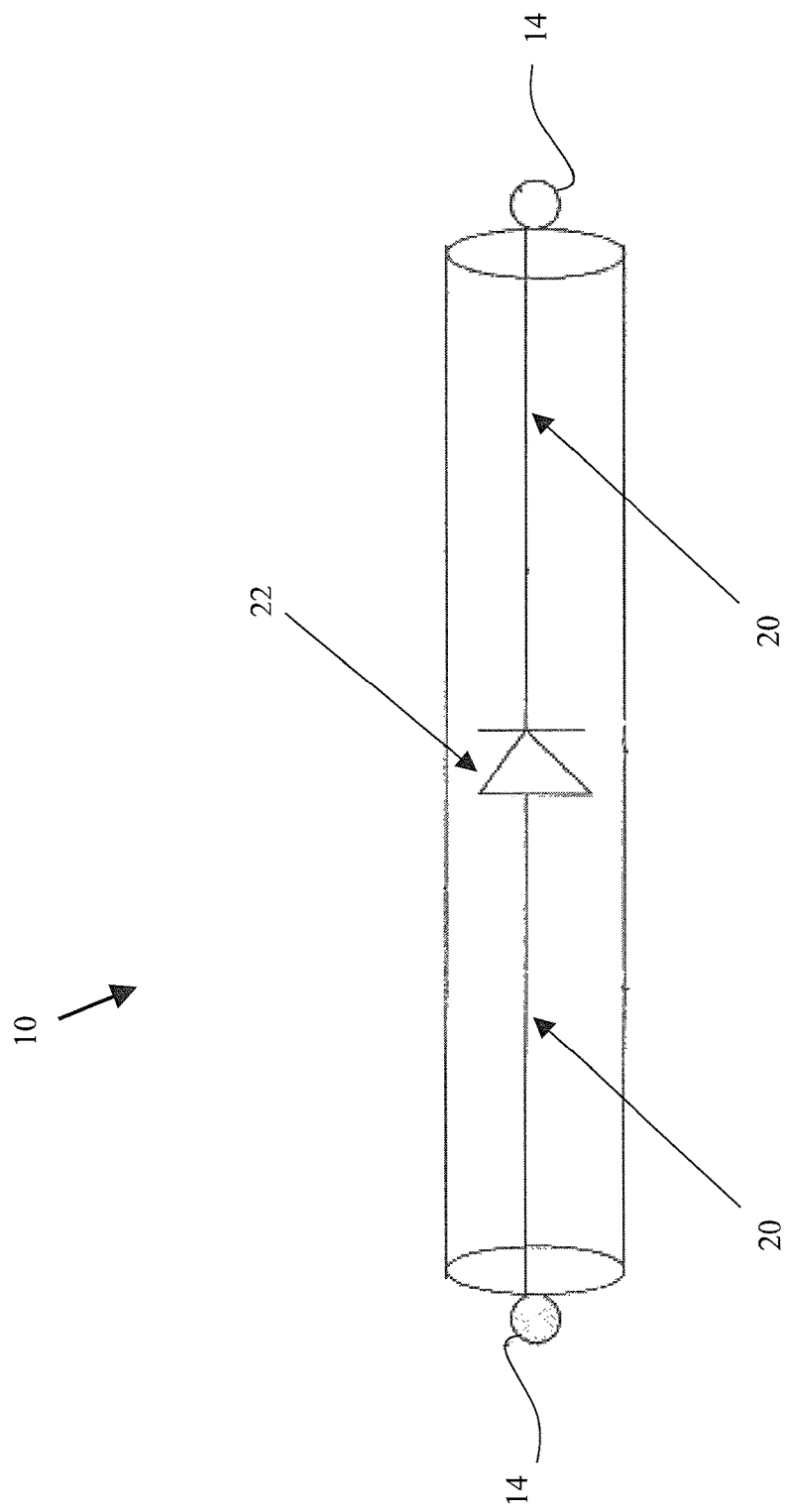
FIG. 2 shows the arrangement of the electronic components of the implant according to a first embodiment.

FIG. 2 shows the electronic components accommodated in the interior of the cylindrical insulating implant housing according to an especially simple design variant.

The focus in FIGS. 2 to 7 is directed in particular at the electronic components of the implant, but it should be pointed out here that the electronic components may be accommodated in the jacket of a tubular insulator as well as in an elongated insulating housing without a continuous lumen.

The electrodes shown in FIGS. 2 to 7 are likewise embodied as ball electrodes. However, this is not to be interpreted as restrictive for the present invention and essentially any type of electrode may be used with each embodiment variant.

According to the embodiment variant shown in FIG. 2, two ball electrodes 14, each connected to an electric feeder line 20, are arranged on the two longitudinal ends of the implant. The feeder lines are in turn connected to the two terminals of a diode 22.

The feeder lines 22 function as antennas, which are designed so that the frequency of the therapeutic energy to be injected preferably corresponds to the resonant frequency. The injected high frequency is rectified and demodulated by the diode 22 and leads to the two electrode poles 14 for applying a pulsed voltage.

In the event of treatment, the implant 10 is positioned in the patient's body, so that the electrode poles 14 of the body tissue to be treated are contacted.

Figure 3:
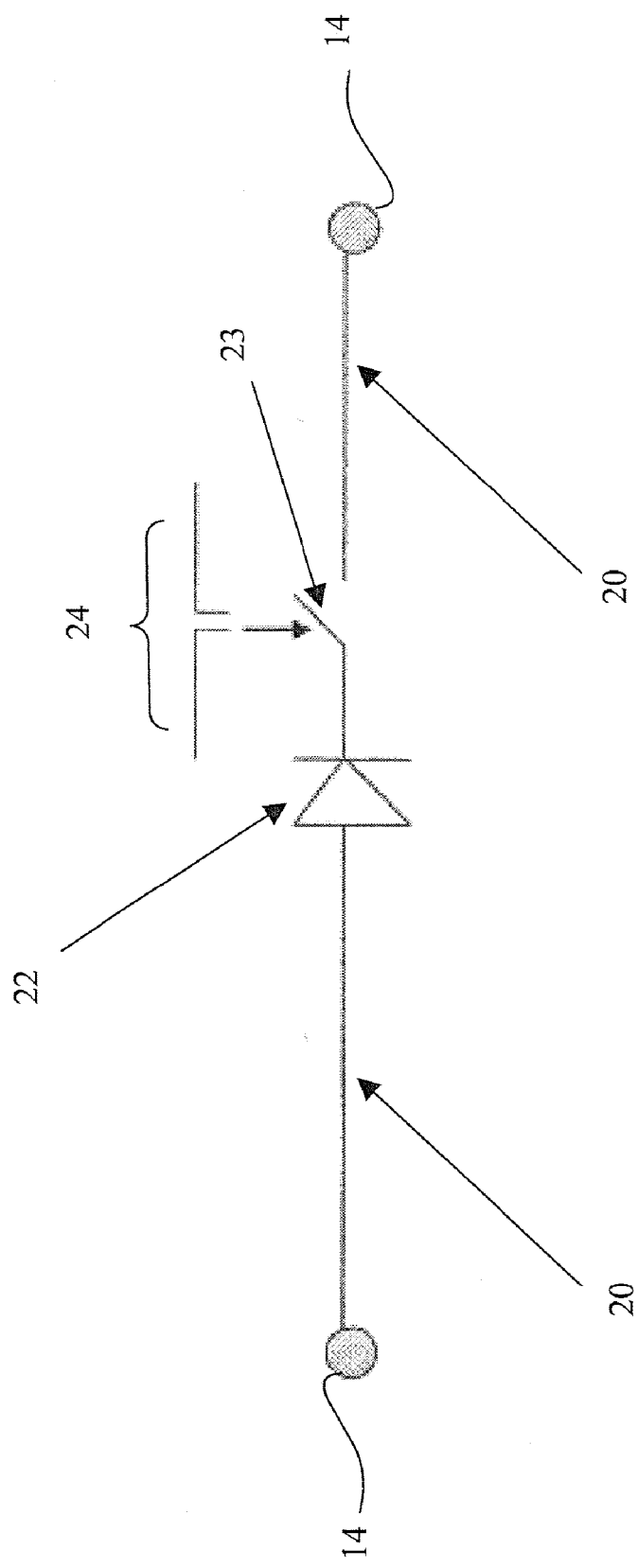
FIG. 3 shows the arrangements of the electronic components of the implant according to a second embodiment having an enable device.

FIG. 3 shows an arrangement of the electronic components of the implant similar to that shown in FIG. 2, having two electrode poles 14, which are connected to the two terminals of a diode 22 via the electric feeder lines 20. According to this embodiment, an enable device 23 is arranged between the terminal of the diode 22 on the output end and the corresponding electric feeder line 20; this enable device is designed to either enable or to block a voltage applied to the electrode poles 14 during operation. This already shows that another antenna 24 is provided for operation of the enable device 23.

Figure 4:
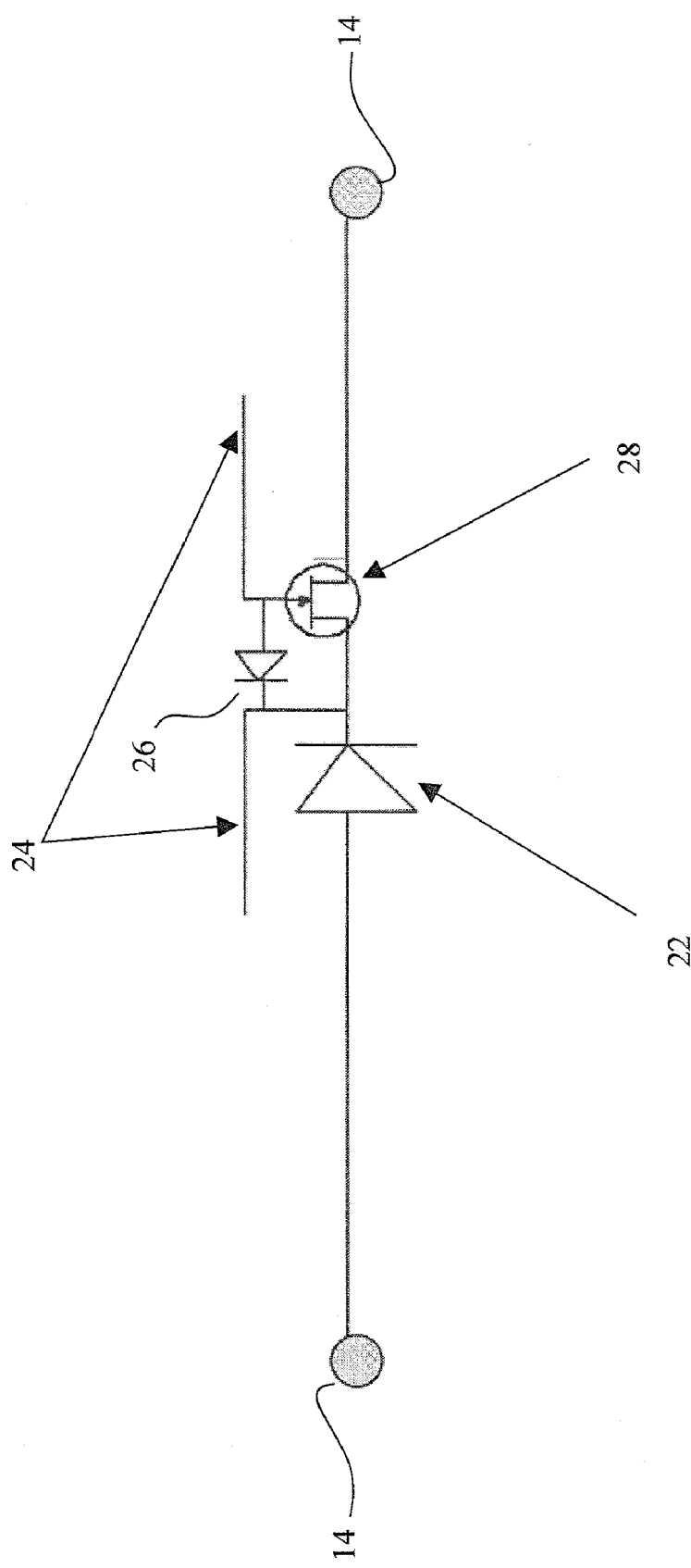
FIG. 4 shows the arrangements of the electronic components of the implant according to the second embodiment, whereby the enable device is embodied as a field effect transistor.

FIG. 4 shows the arrangement of the electronic components according to the embodiment from FIG. 3, where this shows in detail how the electrode poles 14 are enabled to receive control signals and/or enable codes with the help of the antenna 24.

According to the embodiment variant shown here, a JFET transistor 28 serves as the enable device 23.

The enable device 23 may also be implemented as a reed contact. The control is then accomplished not via an additional antenna but instead through a magnetic field acting from the outside and modulated by the external control unit. Instead of a reed contact, other magnetic field-sensitive components may also be used, e.g., components having a giant magnetoresistance (GMR), anisotropic magnetoresistance (AMR), colossal magnetoresistance (CMR) or tunnel magnetoresistance (TMR). Furthermore, the enable device 23 may also be controlled via a piezoelectric transformer. The control signal is injected via mechanical vibrations. This has the advantage that this approach cannot be disturbed by electromagnetic influences.

To enable the electrode poles 14, in one exemplary embodiment a rectified pulsed voltage is generated with the help of high-frequency control signals and/or enable codes over the antenna 24, which also has a diode 26 for rectification, such that conduction of the JFET between diode 22 and electrode pole 14 is controlled by this voltage. The antenna 24 is tuned to a different frequency than the antenna 20. This prevents therapeutic energy that has been erroneously injected into the antenna 20 from being relayed to the electrode poles 14, which thus prevents unwanted stimulation of the tissue to be treated.

Figure 5:
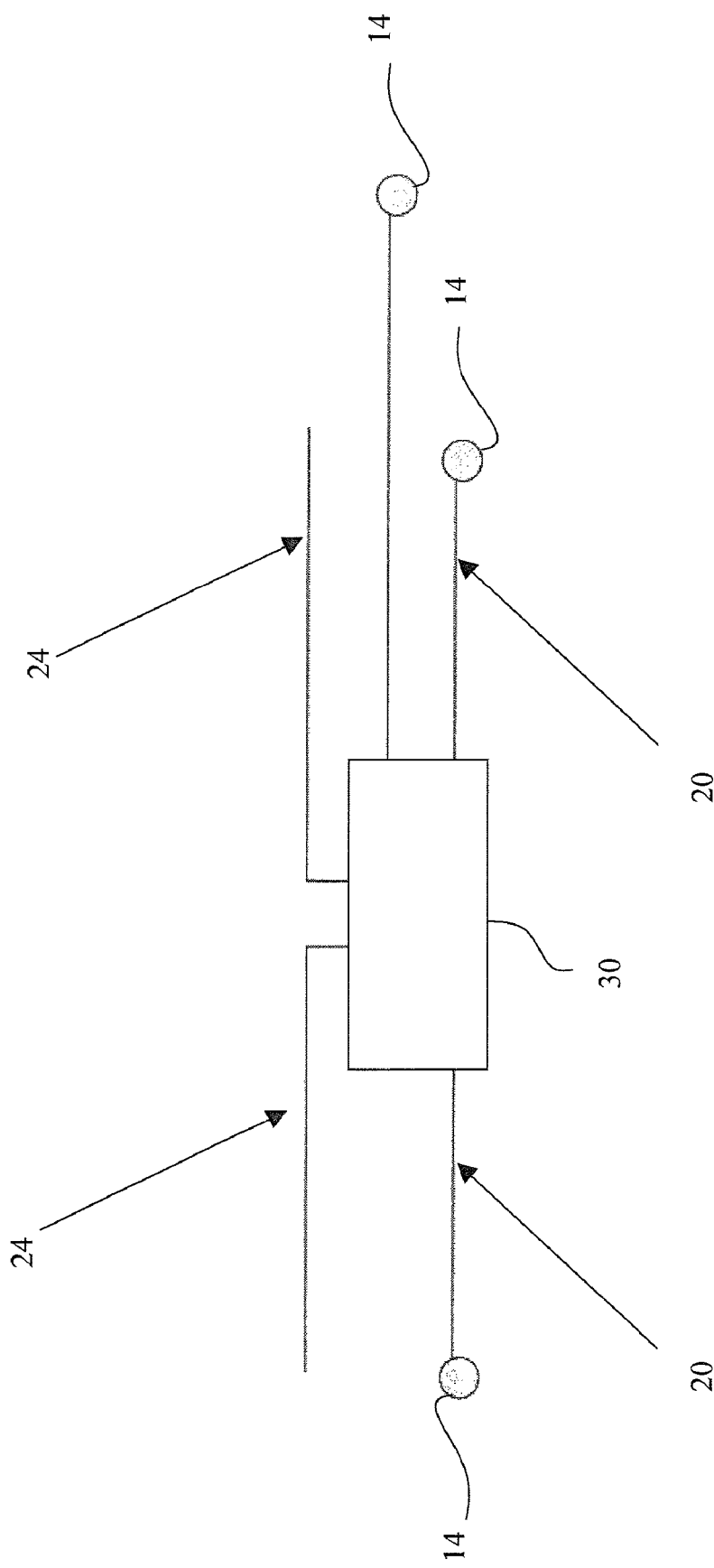
FIG. 5 shows the arrangements of the electronic components of the implant according to a third embodiment with a control unit and three electrode poles.

FIG. 5 shows another embodiment variant of the implant 10 having three electrode poles 14. Instead of the diode 22 and the JFET transistor 28 according to FIG. 4, the variant according to FIG. 5 has a control unit 30, which is designed to perform the rectification and demodulation of an injected high-frequency alternating voltage. At the same time, the control unit 30 also performs the enabling of the three electrodes 14 as a function of the control signals transmitted over the antenna 24 and/or the enable codes.

Figure 8:
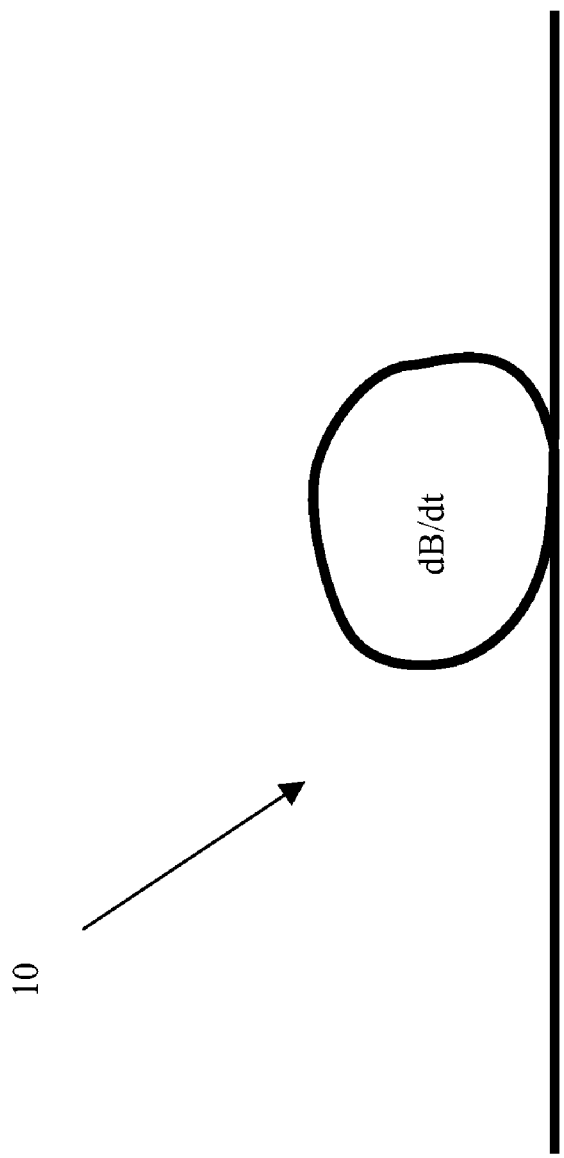
FIG. 8 shows a curved implant that has been bent to form a loop in a patient's body and which functions according to a coil to generate an induction voltage.

The individual components of the control unit 30 are not shown here, but they cause enabling of the electrode poles 14 not to occur until an enable code containing the correct implant-specific individual identifier is received over the antenna 24. The role of the antenna 24 may also be implemented by means of one of the above-mentioned principles (magnetically or ultrasonically). Furthermore, the control signal may also be delivered over the antenna 20 itself without any need for the antenna 24. One approach is to modulate the signal delivering energy into the antenna 20 (e.g., amplitude, frequency or phase modulation). Another approach is to implant the elongated implant, as shown in FIG. 8, so that it forms a loop in which a voltage is induced by a variable magnetic field from the outside (e.g., pulsed), this voltage carrying the control information. The amplitude of the signal induced in this way is to be kept so low that it cannot itself induce stimulation; the control information is then extracted by signal processing in the control unit.

The control unit 30 also has a temporary energy storage mechanism (not shown here), which is designed to continuously supply power to the control unit 30. This energy storage mechanism is designed so that it is charged over the antenna for coupling of the therapeutic energy 20.

Figure 6:
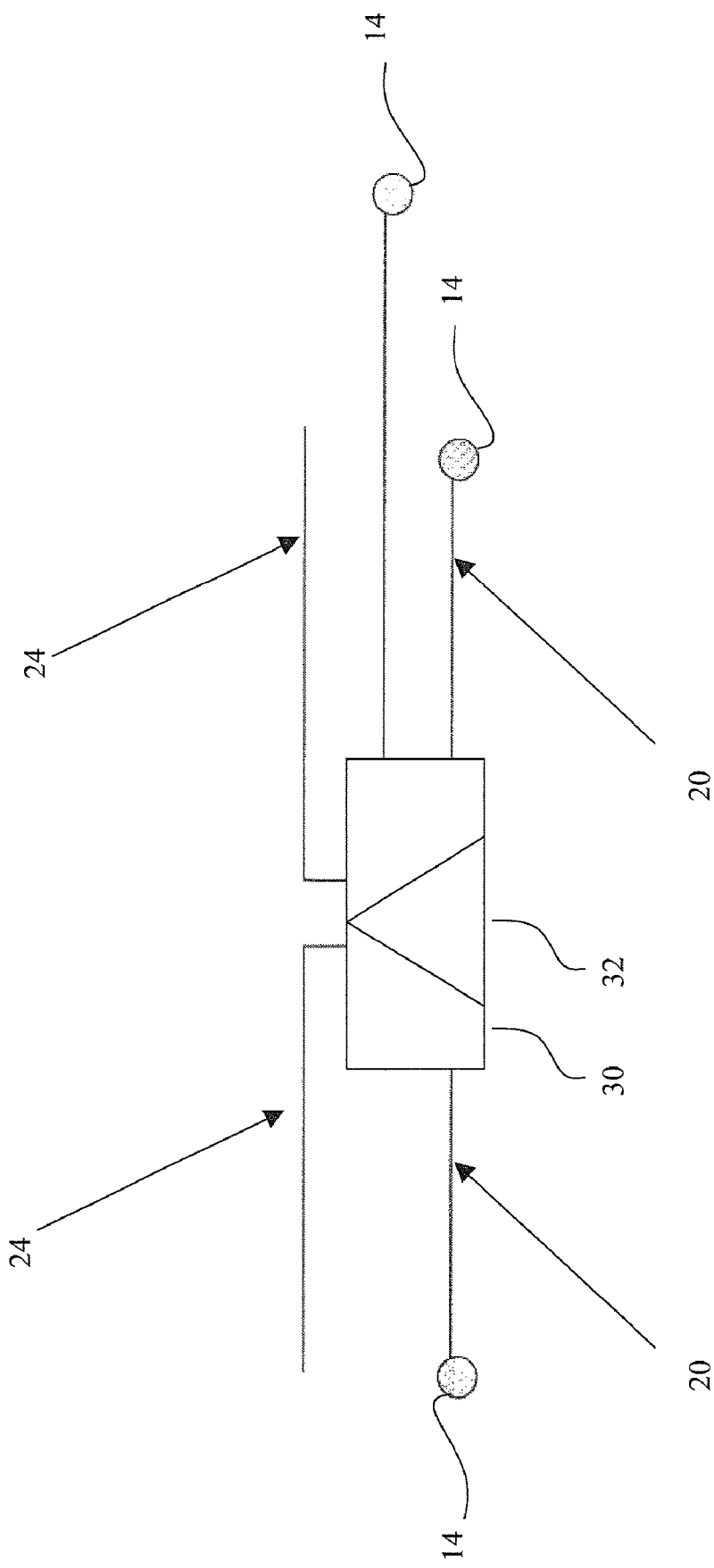
FIG. 6 shows the arrangements of the electronic components of the implant according to a fourth embodiment with a control unit, a measurement device and three electrodes poles.

The embodiment variant of the implant 10 shown in FIG. 6 corresponds in large part to the embodiment variant according to FIG. 5, except that the control unit 30 additionally has a measurement device 32.

The measurement device 32 is designed to measure patient-specific electric pulses (e.g., neural signals) received via the electrode poles 14 and to send them to the outside over the antenna 24. Different sensors (not shown here) measure and/or analyze patient-specific and/or instrument-specific measured data and send them to the outside over the antenna 24.

Figure 7:
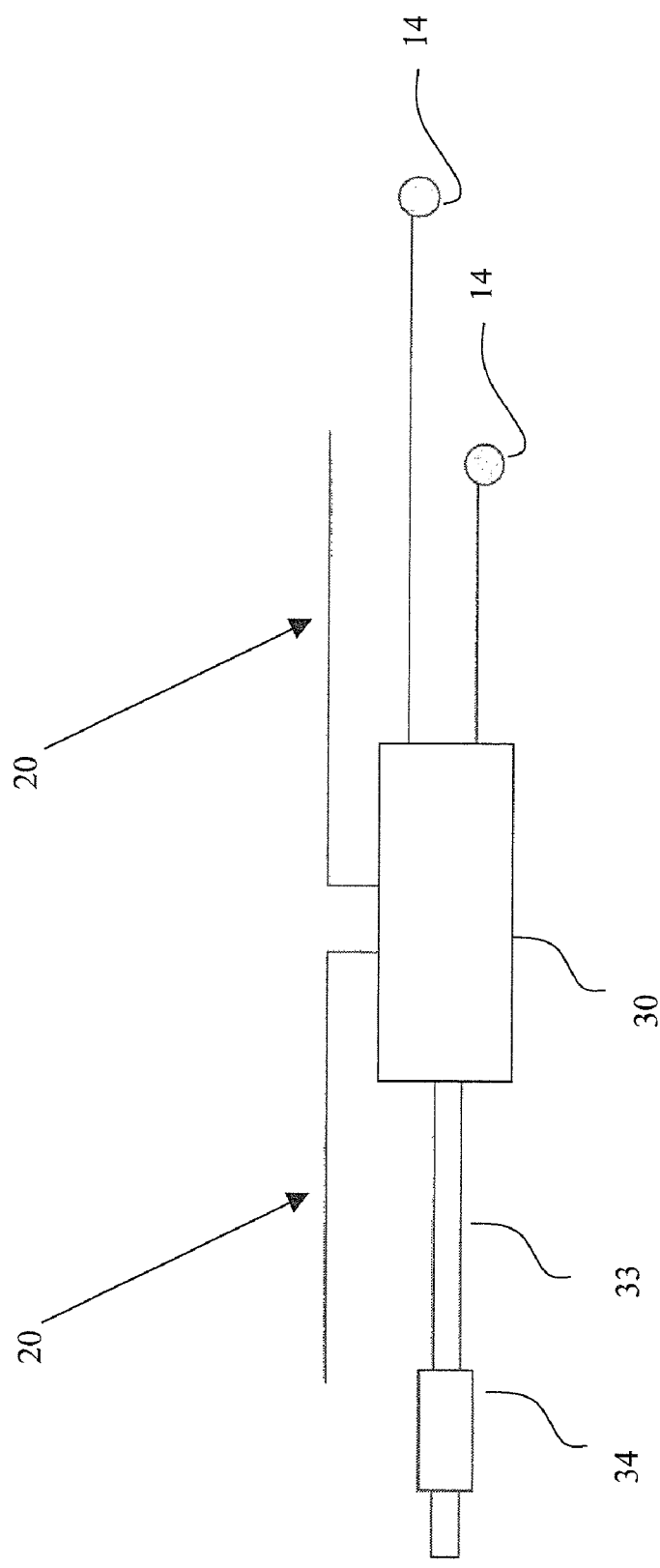
FIG. 7 shows the electronic components of the implant according to a fifth embodiment with a control unit and a terminal for connecting a heart pacemaker.

FIG. 7 shows another embodiment variant of the inventive implant 10, which has a control unit 30 connected to an IS-1 electrode plug 34 by an IPG control line 33, by means of which the implant can also be connected to a traditional heart pacemaker.

What is claimed is:

1. An electrotherapeutic implant (10) for stimulation of body tissue, comprising:
   at least one electric feeder line (20);
   at least two electrode poles (14) which are connected to the at least one electric feeder line (20);
   a demodulation unit (22);
   wherein the at least one electric feeder line (20) is configured as an antenna and is in contact with the demodulation unit (22);
   wherein the electrotherapeutic implant (10) comprises one piece configured as a closed external form and which is further configured to affix at a treatment site and wherein the electrotherapeutic implant (10) further comprises a biocompatible insulation; and,
   at least one terminal (34) configured to electrically and mechanically connect with a heart pacemaker wherein said at least one terminal (34) is electrically coupled with said at least two electrode poles (14) and configured to remain coupled between said electrode poles (14) and heart pacemaker after implantation of said electrotherapeutic implant (10);
   wherein said electrotherapeutic implant (10) is configured to deliver therapeutic energy received from said pacemaker via said at least one terminal (34), and
      from outside of the electrotherapeutic implant (10) over the antenna without storage of the therapeutic energy, to treat a therapeutic target region via the at least two electrode poles (14).

2. The electrotherapeutic implant (10) according to claim 1, further comprising an enable device (23) configured to allow delivery of the therapeutic energy via the at least two electrode poles (14) only when an enable code is received.

3. The electrotherapeutic implant (10) according to claim 2, further comprising:
   a second antenna (24) which is configured to
      receive the enable code required to enable the at least two electrode poles (14) and/or
      receive control signals; and,
   wherein
   an enable code signal frequency
      differs from
   a therapeutic energy frequency.

4. The electrotherapeutic implant (10) according to claim 3, further comprising a control unit (30) that is configured to control a therapeutic sequence wherein a required energy to supply power to the control unit (30) is received over
   the antenna that is configured to receive the therapeutic energy, or
   the second antenna (24) that is configured to receive the control signals and/or the enable code.

5. The electrotherapeutic implant (10) according to claim 2, wherein the enable code required to enable the at least two electrode poles (14) contains an implant-specific individual identifier.

6. The electrotherapeutic implant (10) according to claim 1, further comprising a control unit (30) that is configured to control a therapeutic sequence.

7. The electrotherapeutic implant (10) according to claim 6, further comprising a temporary energy storage mechanism that supplies power to the control unit (30) during the treatment.

8. The electrotherapeutic implant (10) according to claim 1, having a ratio of longitudinal dimension to transverse dimension of greater than or equal to 10.

9. The electrotherapeutic implant (10) according to claim 1, further comprising a control unit coupled with said at least one electric feeder line wherein said control unit is configured for placement within a body comprising the body tissue.

10. The electrotherapeutic implant (10) according to claim 1, wherein the therapeutic energy received is delivered directly to the therapeutic target region with the antenna in contact with the demodulation unit (22) at a first end of the antenna and with the antenna in contact with one of the at least two electrode poles (14) at a second end of the antenna.

11. The electrotherapeutic implant (10) according to claim 1, wherein the demodulation unit (22) is a diode.

12. The electrotherapeutic implant (10) according to claim 1, further comprising:
a second antenna (24); and,
a measurement device (32) that is connected to the antenna or second antenna and wherein the measurement device (32) is configured to transmit patient-specific and/or device-specific measured data to the outside of the electrotherapeutic implant (10) over the antenna or second antenna.

13. A pulse generator for external supply of therapeutic energy to an electrotherapeutic implant according to claim 1, comprising:
a high-frequency generator configured to generate a high-frequency alternating voltage;
at least one antenna over which the therapeutic energy is transmitted as the high-frequency alternating voltage; and,
a control unit configured to generate a control signal that contains information about a desired therapeutic sequence, and,
an enable code to enable the electrotherapeutic implant.

14. The pulse generator according to claim 13, wherein the control unit is configured to receive and analyze and/or store patient-specific measured data and/or instrument-specific measured data sent by the electrotherapeutic implant wherein the electrotherapeutic implant further comprises:
a second antenna (24); and,
a measurement device (32) that is connected to the antenna or second antenna and wherein the measurement device (32) is configured to transmit patient-specific and/or device-specific measured data to the outside of the electrotherapeutic implant (10) over the antenna or second antenna.

* * * * *